(12) United States Patent
Ye et al.

(10) Patent No.: US 11,478,225 B2
(45) Date of Patent: Oct. 25, 2022

(54) APPARATUS AND METHOD FOR PROCESSING ULTRASOUND IMAGE IN VARIOUS SENSOR CONDITIONS

(71) Applicant: KOREA ADVANCED INSTITUTE OF SCIENCE AND TECHNOLOGY, Daejeon (KR)

(72) Inventors: JongChul Ye, Daejeon (KR); Shujaat Khan, Daejeon (KR); Jaeyoung Huh, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 369 days.

(21) Appl. No.: 16/721,015

(22) Filed: Dec. 19, 2019

(65) Prior Publication Data
US 2021/0030400 A1 Feb. 4, 2021

(30) Foreign Application Priority Data

Jul. 30, 2019 (KR) ........................ 10-2019-0092146

(51) Int. Cl.
*A61B 8/08* (2006.01)
*G06T 7/00* (2017.01)

(52) U.S. Cl.
CPC .......... *A61B 8/5207* (2013.01); *A61B 8/5269* (2013.01); *G06T 7/0014* (2013.01); *G06T 2207/10132* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2018/0314985 A1* 11/2018 O'Shea ................... G06N 20/00
2020/0281570 A1* 9/2020 Sato ..................... G01S 7/52028

FOREIGN PATENT DOCUMENTS

KR 10-2001-0077197 A 8/2001
KR 10-2018-0070873 6/2018

OTHER PUBLICATIONS

Khan, Shujaat et al., "Universal Deep Beamformer for Variable Rate Ultrasound Imaging," Department of Bio and Brain Engineering, Korea Advanced Institute of Science and Technology, Jan. 7, 2019.
English Abstract of KR-20180070873, Publication Date: Jun. 27, 2018.

(Continued)

*Primary Examiner* — Leon Flores
(74) *Attorney, Agent, or Firm* — Millen, White, Zelano & Branigan, P.C.; William Nixon

(57) ABSTRACT

An apparatus and method for processing an ultrasound image in various sensor conditions are provided. The method includes receiving a data cube via sensors, transforming the received data cube into focus data through beam focusing, and outputting inphase data and quadrature phase data for the focus data using a neural network corresponding to signal adder and Hilbert transform functions. The method further includes detecting an envelope of the inphase data and the quadrature phase data and reconstructing an ultrasound image for the data cube using log compression.

12 Claims, 10 Drawing Sheets

(56) References Cited

OTHER PUBLICATIONS

Office Action in corresponding Korean 10-2019-0092146 dated Nov. 17, 2020 (pp. 1-8) and english translation thereof.
Khan et al., "Deep Learning-based Universal Beamformer for Ultrasound Imaging", downloaded from internet at https://arxiv.org/pdf/1904.02843.pdf (Jul. 15, 2019).

\* cited by examiner

APPARATUS AND METHOD FOR PROCESSING ULTRASOUND IMAGE IN VARIOUS SENSOR CONDITIONS

CROSS-REFERENCE TO RELATED APPLICATIONS

A claim for priority under 35 U.S.C. § 119 is made to Korean Patent Application No. 10-2019-0092146 filed on Jul. 30, 2019, in the Korean Intellectual Property Office, the entire contents of which are hereby incorporated by reference.

BACKGROUND

Embodiments of the inventive concept described herein relate to technologies of processing ultrasound images, and more particularly, relate to an image processing device for stably performing interpolation in any sampling pattern using a deep learning technology and providing a good-quality image to replace a conventional delay-and-sum (DAS) beamformer.

Excellent temporal resolution with reasonable image quality makes ultrasound (US) modality a first choice for a variety of clinical applications. Moreover, due to its minimal invasiveness from non-ionizing radiations, US is an indispensable tool for some clinical applications such as cardiac, fetal imaging, etc.

The basic imaging principle of US imaging is based on the time-reversal, which is based on a mathematical observation that the wave operator is self-adjoint. In other words, the wave operator is invariant under time transformation $t \rightarrow -t$, and the positions of the sources and receivers may be swapped. Therefore, it is possible to reverse a wave from the measurement positions and different control times to the source locations and the initial time. Practically, this is done by back-propagating the measured data, after the delay transformation $t \rightarrow t_{max} - t$, through adjoint wave and adding all the contributions.

For example, in focused B-mode US imaging, the return echoes from individual scan line are recorded by the receiver channels, after which delay-and-sum (DAS) beamformer applies the time-reversal delay to the channel measurement and additively combines them for each time point to form images at each scan line.

Despite the simplicity, a large number of receiver elements are often necessary in time reversal imaging to improve the image quality by reducing the side lobes. Similarly, high-speed analog-to-digital converters (ADCs) should be used. This is because the mathematical theory of time reversal is derived assuming that the distance between consecutive receivers is taken to be less than half of the wavelength and the temporal scanning is done at a fine rate so that the relative difference between consecutive scanning times is very small. Therefore, with the limited number of receive channels and ADC resolution, DAS beamformer suffers from reduced image resolution and contrast.

To address this problem, various adaptive beamforming techniques have been developed over the several decades. The main idea of adaptive beamforming is to change the receive aperture weights based on the received data statistics to improve the resolution and enhance the contrast. For example, one of the most extensively studied adaptive beamforming techniques is the Capon beamforming, also known as the minimum variance (MV) beamforming. The aperture weight of Capon beamfomer is derived by minimizing the side lobe while maintaining the gain at the look-ahead direction. Unfortunately, Capon beamforming is computational heavy for practical use due to the calculation of the covariance matrix and its inverse. Moreover, the performance of Capon beamformer is dependent upon the accuracy of the covariance matrix estimate. To reduce the complexity, many improved version of MV beamformers have been proposed. Some of the notable examples include the beamspace adaptive beamformer, multi-beam Capon based on multibeam covariance matrices. To improve the robustness of Capon beamformer, parametric form of the covariance matrix calculation with iterative update was also proposed rather than calculating the empirical covariance matrix.

However, Capon beamformer and its variants are usually designed for uniform array, so it is difficult to use for the subsampled sparse array that is often used to reduce the power consumption and data rate. To address this, compressed sensing (CS) approaches have been recently studied. An existing study proposed a point-spread-functions based sensing matrix for CS reconstruction. However, the accurate measurement of the spatially varying point spread function is difficult, which limits the resolution for in vivo experiments. In other existing studies, compressive beamforming methods were proposed. But these approaches usually require changes of ADC part of hardware.

Recently, inspired by the tremendous success of deep learning, many researchers have investigated deep learning approaches for various inverse problems. An existing study proposed a machine learning method to identify and remove reflection artifacts in photoacoustic channel data. Another existing study proposed a frequency domain deep learning method for suppressing off-axis scattering in ultrasound channel data. In another existing study, a deep neural network is designed to estimate the attenuation characteristics of sound in human body. In other existing studies, ultrasound image denoising method is proposed for the B-mode and single angle plane wave imaging, respectively. Rather than using deep neural network as a post processing method, other existing studies use deep neural networks for the reconstruction of high-quality US images from a limited number of RF data. The existing study uses deep neural network for coherent compound imaging from a small number of plane wave illumination. In focused B-mode ultrasound imaging, the existing studies employ the deep neural network to interpolate the missing RF-channel data with multiline acquisition for accelerated scanning and to block artifacts in multiline acquisition and transmission scheme.

While these recent deep neural network approaches provide impressive reconstruction performance, the current design is not universal in the sense that the designed neural network cannot completely replace a DAS beamformer, since they are designed and trained for specific acquisition scenario. Similar limitation exists in the classical MV beamformer, since the covariance matrix is determined by the specific detector geometry, which is difficult to adapt to dynamically varying sparse array.

SUMMARY

Embodiments of the inventive concept provide an image processing device for stably performing interpolation in any sampling pattern using a deep learning technology and providing a good-quality image to replace a conventional delay-and-sum (DAS) beamformer and a method therefor.

According to an exemplary embodiment, a method for processing an ultrasound image may include receiving a data cube via sensors, transforming the received data cube into focus data through beam focusing, and outputting inphase data and quadrature phase data for the focus data using a neural network corresponding to signal adder and Hilbert transform functions.

The method may further include detecting an envelope of the inphase data and the quadrature phase data and reconstructing an ultrasound image for the data cube using log compression.

The neural network may perform interpolation independently of a sampling pattern to output the inphase data and the quadrature phase data for reconstructing a high-quality ultrasound image.

The neural network may be trained using a data cube using at least three or more depths to generate a learning model corresponding to the signal adder and Hilbert transform functions and output the inphase data and the quadrature phase data for the focus data using the learning model.

The neural network may include a convolutional framelet-based neural network.

The neural network may include a bypass connection from an encoder part to a decoder part.

According to an exemplary embodiment, a method for processing an ultrasound image may include receiving a data cube via sensors, transforming the received data cube into focus data through beam focusing, adding signals of the transformed focus data, and outputting inphase data and quadrature phase data for focus data of the added signal using a neural network corresponding to a Hilbert transform function.

According to an exemplary embodiment, an apparatus for processing an ultrasound image may include a reception unit that receives a data cube via sensors, a transform unit that transforms the received data cube into focus data through beam focusing, and an output unit that outputs inphase data and quadrature phase data for the focus data using a neural network corresponding to signal adder and Hilbert transform functions.

The apparatus may further include a reconstruction unit that detects an envelope of the inphase data and the quadrature phase data and reconstructs an ultrasound image for the data cube using log compression.

The neural network may perform interpolation independently of a sampling pattern to output the inphase data and the quadrature phase data for reconstructing a high-quality ultrasound image.

The neural network may be trained using a data cube using at least three or more depths to generate a learning model corresponding to the signal adder and Hilbert transform functions and output the inphase data and the quadrature phase data for the focus data using the learning model.

The neural network may include a convolutional framelet-based neural network.

The neural network may include a bypass connection from an encoder part to a decoder part.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
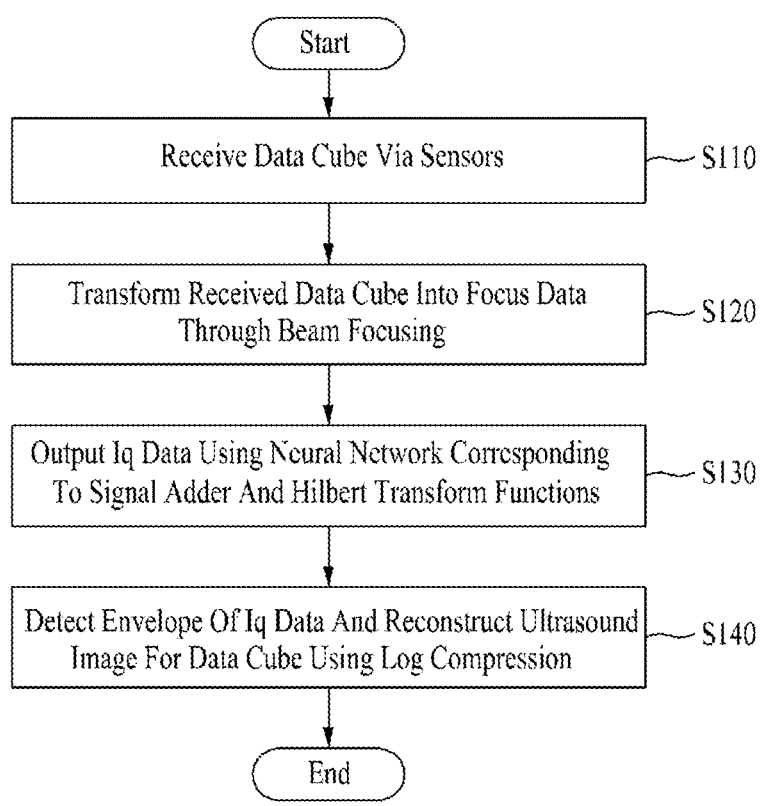
FIG. 1 is an operational flowchart illustrating a method for processing an ultrasound image according to an embodiment of the inventive concept.

Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other components, steps, operations, and/or elements other than stated, components, steps, operations, and/or elements but do not exclude presence of additional elements.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Hereinafter, a description will be given in detail of exemplary embodiments of the inventive concept with reference to the accompanying drawings. Like reference numerals are used for the same components shown in each drawing, and a duplicated description of the same components will be omitted.

A general method for generating an ultrasound image is as follows. A signal returned after a signal is emitted may be received via a sensor and the received signal may be applied to a delay-and-sum (DA) beamformer. A more simplified method is required to implement a high-speed ultrasound imaging system, a low-power ultrasound imaging system, or the like, and this results in deterioration in image quality.

To address such a problem, embodiments of the inventive concept may be the gist of stably performing interpolation in any sampling pattern using a deep learning technology and providing a good-quality image to replace a conventional DAS beamformer.

Herein, embodiments of the inventive concept may perform stable interpolation in any sampling pattern using a single neural network without applying another neural network for each sampling pattern, thus reconstructing a high-quality ultrasound image independently of a sampling pattern.

In this case, a neural network used in embodiments of the inventive concept may include a convolutional neural network (CNN) or a convolutional framelet-based neural network and may include a multi-resolution neural network. In addition, the neural network may include a bypass connection from an encoder part to a decoder part.

In addition, in embodiments of the inventive concept, a single beamformer may generate high-quality images robustly for various detector channel configurations and subsampling rates. The main innovation of a universal deep beamformer in embodiments of the inventive concept comes from exponentially increasing expressiveness that is one of the most exciting properties of deep neural network. For example, the existing study showed that for every natural number k there exists a ReLU network with $k^2$ hidden layers and total size of $k^2$, which may be represented by $1/2k^{k+1}-1$ neurons with at most k-hidden layers. All these results agree that the expressive power of deep neural networks increases exponentially with the network depth. Thanks to the exponential large expressiveness with respect to depth, a deep neural network beamformer according to an embodiment of the inventive concept may learn the mapping to images from various sub-sampled RF measurements, and may exhibit superior image quality for all sub-sampling rates. As the network is trained to learn the mapping from the sub-sampled channel data to the B-mode images from full rate DAS images, an embodiment of the inventive concept may utilize the fully sampled RF data furthermore to improve the image contrast even for the full rate.

FIG. 1 is an operational flowchart illustrating a method for processing an ultrasound image according to an embodiment of the inventive concept.

Referring to FIG. 1, in S110 of the method for processing the ultrasound image according to an embodiment of the inventive concept, ultrasound raw data, for example, a data cube may be received via sensors included in an ultrasound imaging system, that is, sensors included in a receiver, for example, 16 receiver sensors.

Herein, the data cube may include an index or identification number of each of the receiver sensors, a transmit event (TE), and depth information.

When the data cube is received in S110, in S120, the received data cube may be transformed into focus data through beam focusing.

When the received data cube is transformed into the focus data in S120, in S130, inphase data and quadrature phase data for the focus data may be output using a neural network corresponding to signal adder and Hilbert transform functions.

Herein, the neural network may include a convolutional neural network (CNN), a convolutional framelet-based neural network, or a multi-resolution neural network, and may include a bypass connection from an encoder part for performing encoding to a decoder part for performing decoding.

The convolutional framelet is a manner of representing an input signal using a local basis and a non-local basis. Detailed contents of the convolutional framelet are described in Korean Patent Application No. 10-2018-0070873 filed by the inventor of the present invention.

In addition, the neural network may perform interpolation independently of a sampling pattern to output inphase data and quadrature phase data for reconstructing a high-quality ultrasound image. Such a neural network may be trained using a predetermined training data set to generate a learning model corresponding to the signal adder and Hilbert transform functions. For example, the neural network may be trained using a data cube including at least three or more depths to generate the learning model corresponding to the signal adder and Hilbert transform functions and output inphase data and quadrature phase data for focus data using the generated learning model.

When the IQ data, that is, the inphase data and the quadrature phase data are output over the neural network in S130, in S140, an envelope of the inphase data and the quadrature phase data may be detected and an ultrasound image for the data cube may be reconstructed using log compression.

A description will be given in detail of the method according to an embodiment of the inventive concept with reference to FIGS. 2 to 6B.

Adaptive Beamforming

The standard non-gain compensated delay-and-sum (DAS) beamformer for the l-th scan line at the depth sample n may be expressed as Equation 1 below.

$$z_l[n] = \frac{1}{J}\sum_{j=0}^{J-1} x_{l,j}[n-\tau_j[n]] = \frac{1}{J}1^T y_l[n], \quad \text{[Equation 1]}$$

$$l = 0, \ldots, L-1$$

τ denotes the transpose, $x_{l,j}[n]$ denotes the RF echo signal measured by the j-th active receiver element from the transmit event (TE) for the l-th scan line, and J denotes the number of active receivers, and $\tau_j[n]$ denotes the dynamic focusing delay for the j-th active receiver elements to obtain the l-th scan line. Furthermore, $y_l[n]$ refers to the scan line dependent time reversed RF data defined by Equation 2 below.

$$y_l[n] = [y_{l,0}[n]\ y_{l,1}[n] \ldots y_{l,j-1}[n]]^T, y_{l,j}[n] := x_{l,j}[n-\tau_j[n]] \quad \text{[Equation 2]}$$

Herein, l denotes a length of one J column-vector.

This averaging of the time-delayed element-outputs extracts the (spatially) low-frequency content that corresponds to the energy within one scan resolution cell (or main lobe). Reduced side lobe leakage at the expense of a wider resolution cell may be achieved by replacing the uniform weights by tapered weights $w_{l,j}[n]$ and may be represented as Equation 3 below.

$$z_l[n] = \sum_{j=0}^{J-1} w_{l,j}[n] y_{l,j}[n] = w_l[n]^T y_l[n] \quad \text{[Equation 3]}$$

Herein, $w_l[n] = [w_{l,0}[n]\ w_{l,1}[n] \ldots w_{l,J}[n]]^T$.

In adaptive beamforming, the objective is to find the $w_l$ that minimizes the variance of $z_l$, subject to the constraint that the gain in the desired beam direction equals unity. The minimum variance (MV) estimation task may be represented as Equation 4 below and may be formulated as Equations 5-7 below.

$$\underset{w_l[n]}{\text{minimize}}\ E[|z_l[n]|^2] = \underset{w_l[n]}{\min} w_l[n]^T R_l[n] w_l[n] \quad \text{[Equation 4]}$$

$$\text{subject to } w_l[n]^H a = 1$$

E[·] denotes the expectation operator, and a denotes a steering vector, which is composed of ones when the received signal is already temporally aligned, and R[n] denotes a spatial covariance matrix.

The spatial covariance matrix may be expressed as Equation 5 below.

$$R_l[n]=E[y_l[n]^* y_l[n]]$$ [Equation 5]

Then, $w_l[n]$ may be obtained by the Lagrange multiplier method and expressed as Equation 6 below.

$$w_l[n] = \frac{R_l[n]^{-1} a}{a^H R_l[n]^{-1} a}$$ [Equation 6]

In practice, $R_l[n]$ must be estimated with a limited amount of data. A widely used method for the estimation of $R_l[n]$ is spatial smoothing (or subaperture averaging), in which the sample covariance matrix is calculated by averaging covariance matrices of K consecutive channels in the J receiving channels, as expressed as Equations 7 and 8 below.

$$\tilde{R}_l[n] = \frac{1}{J-K+1} Y_l[n] Y_l^T[n]$$ [Equation 7]

$$Y_l[n] = \begin{bmatrix} y_{l,0}[n] & \cdots & y_{l,J-K}[n] \\ \vdots & & \vdots \\ y_{l,K-1}[n] & \cdots & y_{l,J-1}[n] \end{bmatrix}$$ [Equation 8]

There is an invertible matrix if K≤J/2. To further improve the invertibility of the sample covariance matrix, another method usually called diagonal loading is often used by adding additional diagonal terms.

One of the problems with the MV beamforming technique employed in a medical ultrasound imaging system is that the speckle characteristics tend to be different from those of conventional DAS beamformed images. MV beamformed images tend to look slightly different from conventional DAS B-mode images in that the speckle region appears to have many small black dots interspersed. To overcome this problem, a temporal averaging method that averages $\tilde{R}$ along the depth direction is used, which is expressed as Equation 9 below.

$$\tilde{R}_l[n] = \frac{1}{2L+1} \frac{1}{J-K+1} \sum_{l=-L}^{L} Y_l[n+l] Y_l^T[n+l]$$ [Equation 9]

Another method to estimate the covariance matrix in MV is so-called multibeam approach. In this method, the weight vector is estimated using empirical covariance matrices that are formed to use phase-based (narrowband) steering vectors to extract the adaptive array weights from it.

Hereinafter, a description will be given of an embodiment of the inventive concept.

Figure 2A:
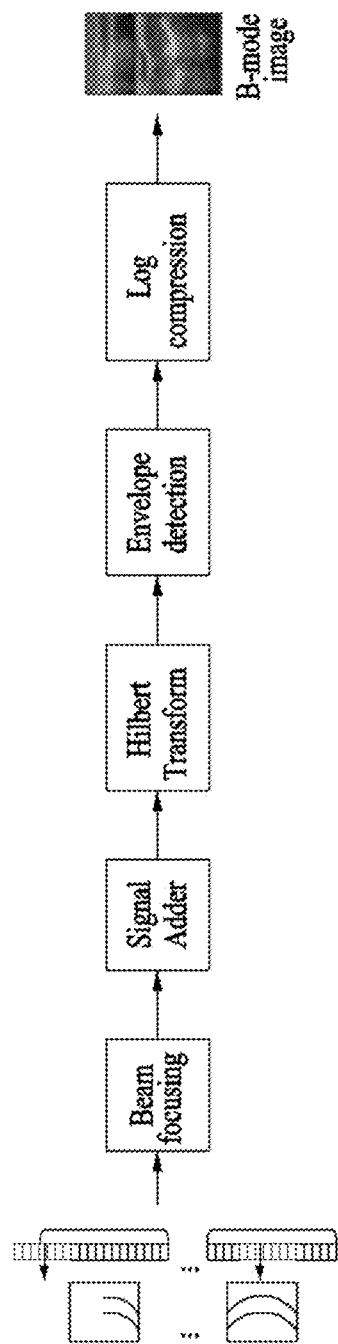
FIGS. 2A and 2B are drawings illustrating ultrasound imaging pipelines.
Figure 2B:
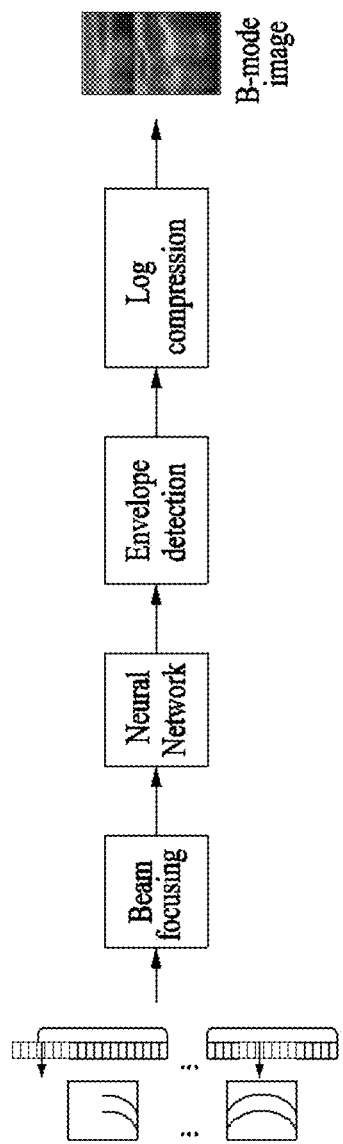

1) Image reconstruction pipeline: FIGS. 2A and 2B are drawings illustrating ultrasound imaging pipelines. FIG. 2A illustrates the conventional US image reconstruction pipeline. Here, the reflected sound waves in the medium are detected by the transducer elements. Each measured signal is time reversed based on the traveled distance to perform beam-focusing. The focused signals are later added. In an embodiment of the inventive concept, the adaptive beamformer may be used for providing adaptive summation of the time-reversed echoes. This is then followed by the Hilbert transform to detect the envelope of the beam. In particular, the envelop is determined by calculating the absolute value of the inphase and quadrature phase signals generated from the Hilbert transform. Finally, the log compression may be applied to generate the B-mode images.

On the other hand, the goal according to an embodiment of the inventive concept is to replace the signal adder and the Hilbert transform step by step with a convolutional neural network (CNN) as shown in FIG. 2B. Time reversal part is still based on the physical delay calculation, since this is the main idea of the time reversal algorithms Envelop detection and log compression are just a simple point-wise operation, so the neural network is not necessary. Therefore, an embodiment of the inventive concept is to basically replace the core beamformer and reconstruction engine with a data-driven way CNN. 2) Universal Deep Beamformer: The basic idea of adaptive beamformer is to estimate the array weight from the data to estimate $z_l[n]$, which changes with respect to the scan line index l and the depth n. In the conventional adaptive beamformer, this estimation is usually done based on the linear weight model calculated from the empirical covariance. However, this linear model is usually based on restricted assumption, such as zero mean, Gaussian noise, and the like, which may limit the fundamental performance of the adaptive beamformer. Moreover, nonlinear beamforming methods have been recently proposed to overcome the limitation of linear model. Another important step after the beamforming is the Hilbert transform to obtain analytic representation. More specifically, Hilbert transform gives the analytic representation of a signal u(t) and may be expressed as Equation 10 below.

$$z_l^a[n]=z_l[n]+\iota H(z_l)[n]$$ [Equation 10]

Herein, $\iota=\sqrt{-1}$ and H denotes the Hilbert transform. $z_l^a[n]$ often referred to as the inphase (I) and quadrature phase (Q) representation. To implement the Hilbert transform, discrete convolution operation is usually performed for each scan line along the depth direction.

One of the main key ideas of the method according to an embodiment of the inventive concept is a direct estimation of the beamformed and Hilbert transformed signal $z_l^a[n]$ directly from the time-reverse signal $y_l[n]$ using the convolutional neural network. To exploit the redundancies along the scan line direction, rather than estimating the beamformed signal for each scan line, an embodiment of the inventive concept is interested in estimating the beamformed and Hilbert transformed signal at whole scan line, that is, $z^a[n]=[z_0^a[n]\ldots z_{L-31\ 1}^a[n]]^T$.

Furthermore, to deal with the potential blurring along the depth, an embodiment of the inventive concept is interested in exploiting the time reversed signal at three depth coordinates, which may be expressed as Equation 11 below.

$$Y[n] = \begin{bmatrix} y_0[n-1] & y_1[n-1] & \cdots & y_{L-1}[n-1] \\ y_0[n] & y_1[n] & \cdots & y_{L-1}[n] \\ y_0[n+1] & y_1[n+1] & \cdots & y_{L-1}[n+1] \end{bmatrix}$$ [Equation 11]

The goal according to an embodiment of the inventive concept is to estimate the nonlinear function $f(W, Y[n])$ like Equation 12 below.

$$z^a[n]=f(\Theta, Y[n])$$ [Equation 12]

Herein, $\Theta$ denotes the trainable CNN parameters.

To generate the complex output, the neural network according to an embodiment of the inventive concept generates the two channel outputs that correspond to the real and image parts. Then, the CNN according to an embodiment of the inventive concept, called deep beamformer (DeepBP), is trained as Equation 13 below.

$$\min_{\Theta} \sum_{i=1}^{T} \sum_{n} \|z^{a(i)}[n] - f(\Theta, Y^{(i)}[n])\|^2 \quad \text{[Equation 13]}$$

Herein, $z^{a(i)}[n]$ denotes the ground-truth I-Q channel data at the depth n from the i-th training data, and $Y^{(i)}[n]$ represents the time-delayed input data formed by Equation 11 above, for example, the sub-sampled time-delayed input data.

The training scheme in an embodiment of the inventive concept is depth-independent so that the same CNN may be used across all depth. Furthermore, as for the target data for the training, an embodiment of the inventive concept may use the standard DAS beamformed data from full detector samples. Because the target data is obtained from various depth across multiple scan lines, the neural network according to an embodiment of the inventive concept may be expected to learn the best parameters on averages. Interestingly, this average behavior may turn out to improve the overall image quality even without any sub-sampling thanks to the synergistic learning from many training data.

Figure 3:
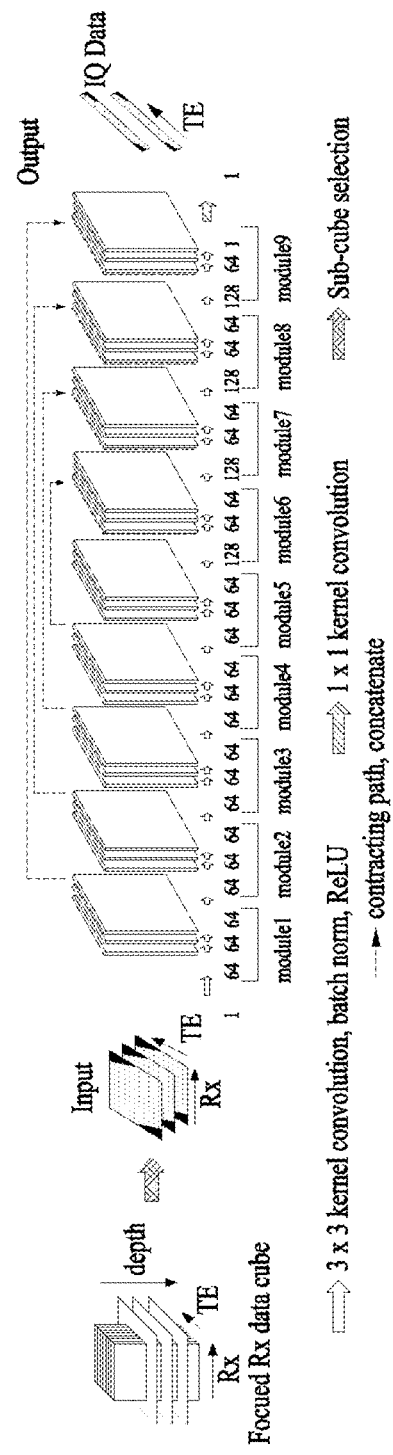
FIG. 3 is a drawing illustrating a block diagram for a CNN-based ultrasound imaging system according to an embodiment of the inventive concept.

FIG. 3 is a drawing illustrating a block diagram for a CNN-based ultrasound imaging system according to an embodiment of the inventive concept. As shown in FIG. 3, an embodiment of the inventive concept may train the model with the 3-D input/output pairs of Rx-TE-Depth data cube as an input and the I-Q data on a single Rx-TE plane as a target.

Data Set

For experimental verification, multiple RF data may be acquired with, a specific system, for example, the E-CUBE 12R US system (Alpinion Co., Korea). For data acquisition, an embodiment of the inventive concept may use a linear array transducer (L3-12H) with a center frequency of 8:48 MHz. The configuration of the probe may be given in Table 1 below.

TABLE 1

| Parameter | Linear Probe |
| --- | --- |
| Probe Model No. | L3-12H |
| Carrier wave frequency | 8.48 MHz |
| Sampling frequency | 40 MHz |
| No. of probe elements | 192 |
| No. of Tx elements | 128 |
| No. of TE events | 96 |
| No. of Rx elements | 64 |
| Elements pitch | 0.2 mm |
| Elements width | 0.14 mm |
| Elevating length | 4.5 mm |

Using a linear probe, an embodiment of the inventive concept may acquire RF data from the carotid area from 10 volunteers. The in-vivo data consists of 40 temporal frames per subject, providing 400 sets of Depth-Rx-TE data cube. The dimension of each Rx-TE plane is 64×96. A set of 30,000 Rx-TE planes is randomly selected from the 4 subject datasets, and data cubes (Rx-TE-depth) are then divided into 25,000 datasets for training and 5000 datasets for validation. The remaining dataset of 360 frames may be used as a test dataset.

In addition, an embodiment of the inventive concept may acquire 188 frames of RF data from the ATS-539 multipurpose tissue mimicking phantom. This dataset may only be used for test purposes and no additional training of CNN is performed on the CNN. The phantom dataset may be used to verify the generalization power of the method according to an embodiment of the inventive concept.

RF Sub-Sampling Scheme

Figure 4:
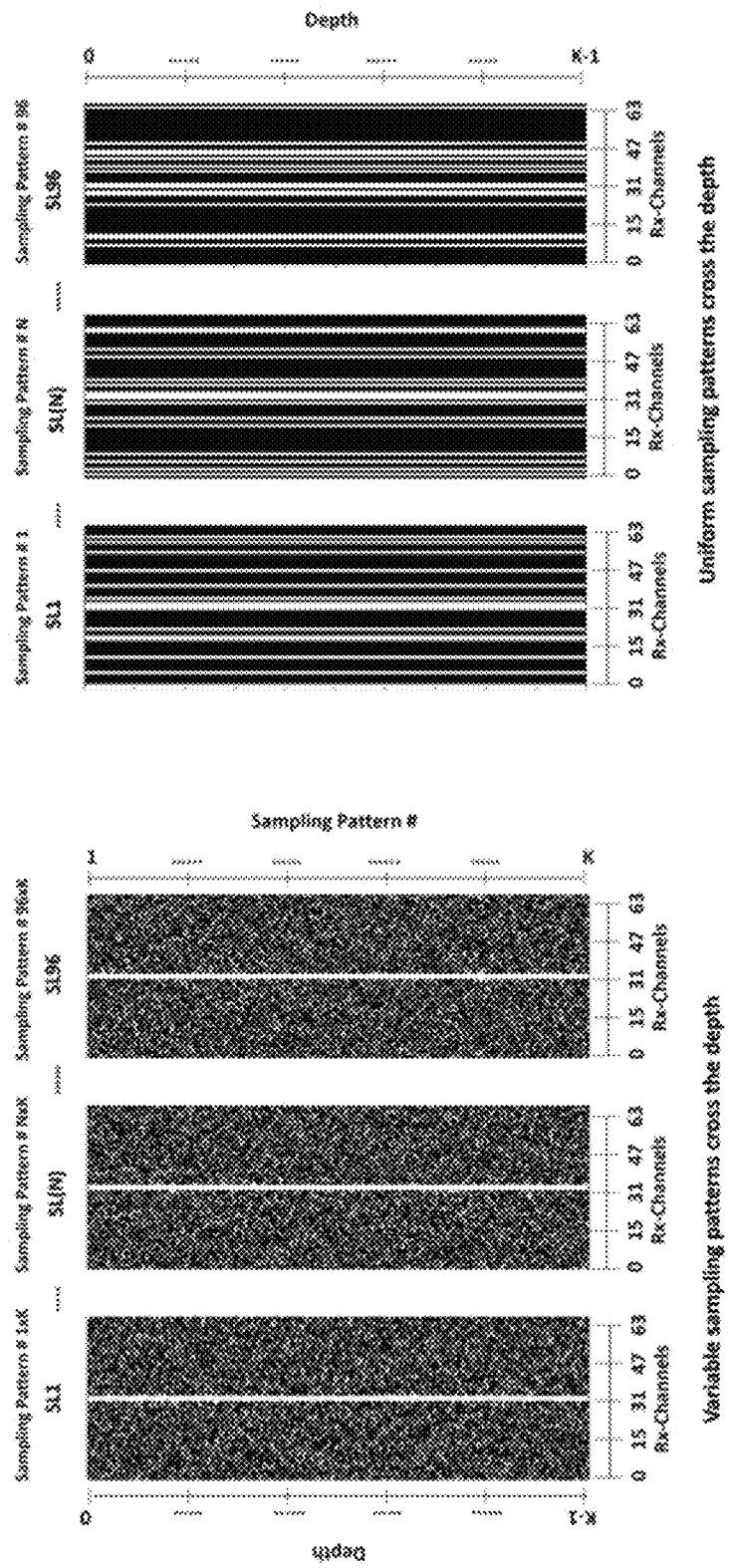
FIG. 4 is a drawing illustrating sampling schemes.

An embodiment of the inventive concept may generate six sets of sub-sampled RF data at different down-sampling rates. In particular, as shown in FIG. 4, an embodiment of the inventive concept may use several sub-sampling schemes using 64, 32, 24, 16, 8 and 4 Rxchannels, and may use two sub-sampling schemes, for example, a variable down-sampling pattern cross the depth and a fixed down-sampling pattern cross the depth.

Because the active receivers at the center of the scan-line obtain RF data from direct reflection, the two channels that are in the center of active transmitting channels may always be included to improve the performance, and remaining channels may be randomly selected from the total 64 active receiving channels. In variable sampling scheme, a different sampling pattern (mask) may be used for each depth plane, whereas, in fixed sampling, the same sampling pattern (mask) may be used for all depth planes. The network may be trained for variable sampling scheme only and both sampling schemes may be used in test phase.

Network Architecture

For all sub-sampling scheme samples, a multi-channel CNN may be applied to 3×64×96 data-cube in the depth-Rx-TE sub-space to generate a 2×3×96 I and Q data in the depth-TE plane. Each of the target IQ data obtained from two output channels may represent real and imaginary parts.

The CNN in an embodiment of the inventive concept may include convolution layers for performing linear transform operation, batch normalization layers for performing normalization operation, rectified linear unit (ReLU) layers for performing nonlinear function operation, and a contracting path connection with concatenation. Specifically, the neural network may consist of 29 convolution layers composed of a batch normalization layer and a ReLU layer except for the last convolution layer. The first 28 convolution layers may use 3×3 convolutional filters (i.e., the 2-D filter has a dimension of 3×3), and the last convolution layer may use a 1×1 filter and may contract the 3×64×96 data-cube from depth-Rx-TE sub-space to 2×3×96 IQ-depth-TE plane.

The network may be implemented with MatConvNet in the MATLAB 2015b environment. Specifically, for network training, the parameters may be estimated by minimizing the $l_2$ norm loss function. The network may be trained using a stochastic gradient descent (SGD) with a regularization parameter of $10^{-4}$. The learning rate may start from $10^{-4}$ and may gradually decrease to $10^{-7}$. The weights may be initialized using Gaussian random distribution with the Xavier method. The number of epochs may be 200 for all down-sampling rates.

Performance Metrics

To quantitatively show the advantages of the deep learning method in an embodiment of the inventive concept, the embodiment of the inventive concept may use the contrast-to-noise ratio (CNR), generalized CNR (GCNR), peak-signal-to-noise ratio (PSNR), structure similarity (SSIM), and the reconstruction time.

The CNR may be measured for the background (B) and anechoic structure (aS) in the image, and may be quantified as Equation 14 below.

$$CNR(B, aS) = \frac{|\mu_B - \mu_{aS}|}{\sqrt{\sigma_B^2 + \sigma_{aS}^2}}$$ [Equation 14]

Herein, $\mu_B$, $\mu_{aS}$ and $\sigma_B$, $\sigma_{aS}$ denote the means and the standard deviations of the background (B) and anechoic structure (aS).

Recently, an improved measure for the contrast-to-noise ratio called generalized-CNR (GCNR) is proposed. The GCNR compares the overlap between the intensity distributions of two regions. The GCNR measure is difficult to tweak and shows exact quality improvement for non-linear beamformers on a fixed scale ranges from zero to one, where one represents no overlap in the distributions of background and region-of-interest (ROI). The GCNR may be defined as Equation 15 below.

$$GCNR(B, aS) = 1 - \int \min\{p_B(x), p_{aS}(x)\} dx$$ [Equation 15]

Herein, x denotes the pixel intensity, pB and paS denote the probability distribution of the background (B) and anechoic structure (aS). When both of distributions are completely independent, then GCNR will be equals to one, whereas, when they completely overlap, then the GCNR will be zero.

The PSNR and the SSIM index may be calculated on reference (F) and Rx sub-sampled ($\tilde{F}$) images of common size n1×n2, and the PSNR and the SSIM index may be represented as Equations 16 and 17 below, respectively.

$$PSNR(F, \tilde{F}) = 10 \log_{10} \left( \frac{n_1 n_2 R_{max}^2}{\|F - \tilde{F}\|_F^2} \right)$$ [Equation 16]

Herein, $\|\cdot\|_F$ denotes the Frobenius norm and $R_{max} = 2^{(\#bits\ per\ pixel)} - 1$ denotes the dynamic range of pixel values, for example, 255.

$$SSIM(F, \tilde{F}) = \frac{(2\mu_F \mu_{\tilde{F}} + c_1)(2\sigma_{F,\tilde{F}} + c_2)}{(\mu_F^2 + \mu_{\tilde{F}}^2 + c_1)(\sigma_F^2 + \sigma_{\tilde{F}}^2 + c_2)}$$ [Equation 17]

Herein, $\mu F$, $\mu \tilde{F}$, $\sigma F$, $\sigma \tilde{F}$, and $\sigma F,\tilde{F}$ denote the means, standard deviations, and cross-covariance for images F and $\tilde{F}$ calculated for a radius of 50 units and denotes the default values of $c_1 = (k_1 R_{max})^2$, $c_2 = (k_2 R_{max})^2$, $k_1 = 0.01$, and $k_2 = 0.03$.

Figure 5A:
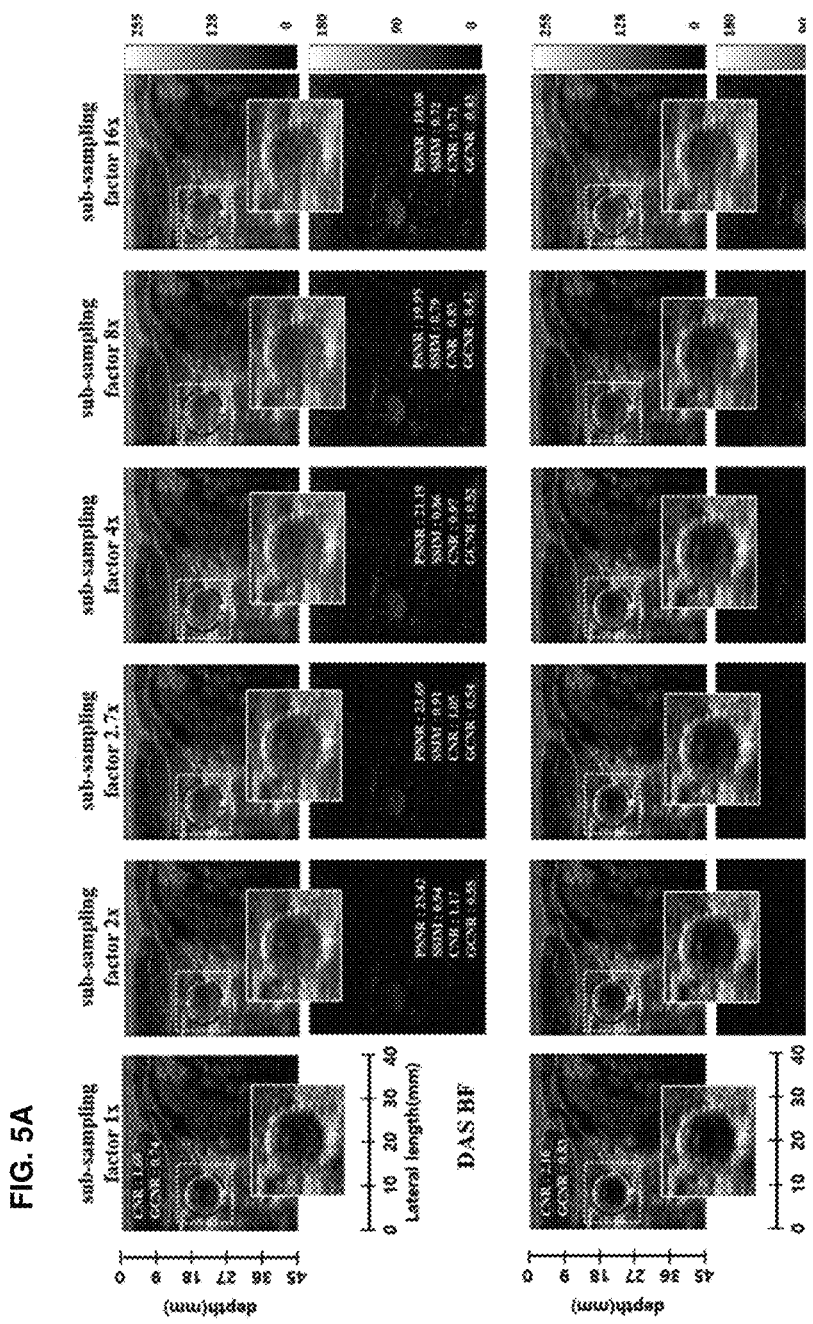
FIGS. 5A and 5B are drawings illustrating reconstruction results of a standard DA beamformer and a method according to an embodiment of the inventive concept for the carotid region with respect to two sub-sampling schemes.
Figure 5B:
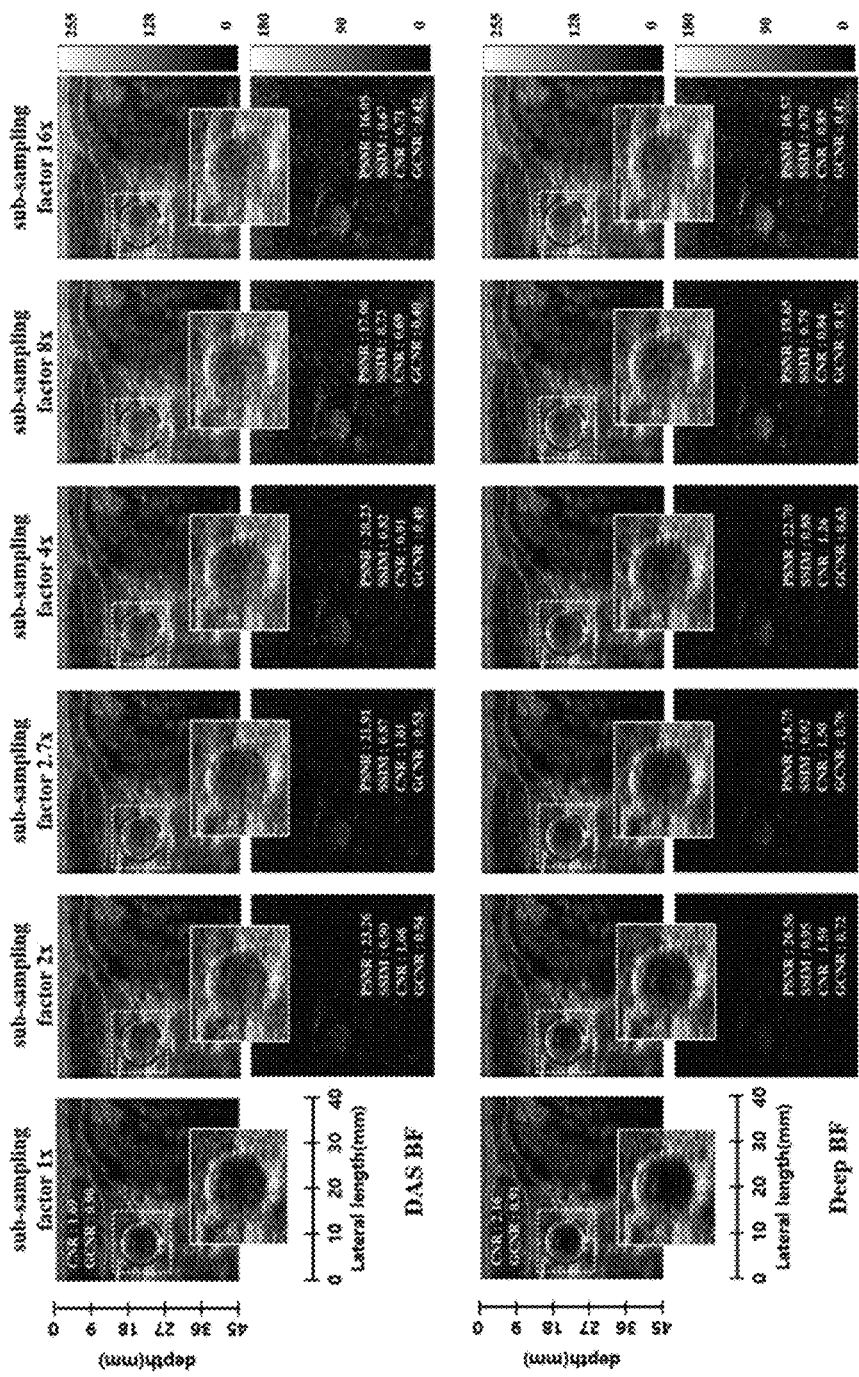

FIGS. 5A and 5B are drawings illustrating reconstruction results of a standard DA beamformer and a method according to an embodiment of the inventive concept for the carotid region with respect to two subsampling schemes. FIGS. 5A and 5B show the results of two in vivo examples for 64, 32, 24, 16, 8, and 4 Rx-channel down-sampling schemes using two sub-sampling schemes, that is, a variable sampling scheme (FIG. 5A) and a fixed sampling scheme (FIG. 5B).

As shown in FIGS. 5A and 5B, because 64 channels are used as full sampled data, this corresponds to 1×, 2×, 2.7×, 4×, 8×, and 16× acceleration. The images are generated using the DeepBF according to an embodiment of the inventive concept and the standard DAS beam-former method. The method according to an embodiment of the inventive concept may improve the visual quality of the ultrasound images by estimating the correct dynamic range and eliminating artifacts for both sampling schemes. As may be observed in FIGS. 5A and 5B, it is evident that under fixed down-sampling scheme, the quality degradation of images is higher than the variable sampling scheme, but the relative improvement in both schemes using the method according to an embodiment of the inventive concept is nearly the same. Furthermore, the method according to an embodiment of the inventive concept successfully reconstructs both the near field region and the far field region with equal efficacy, and only minor structural details are imperceivable. Furthermore, it is remarkable that the CNR and GCNR values are more significantly improved by the method according to an embodiment of the inventive concept than the standard DAS beamforming method.

Figure 6A:
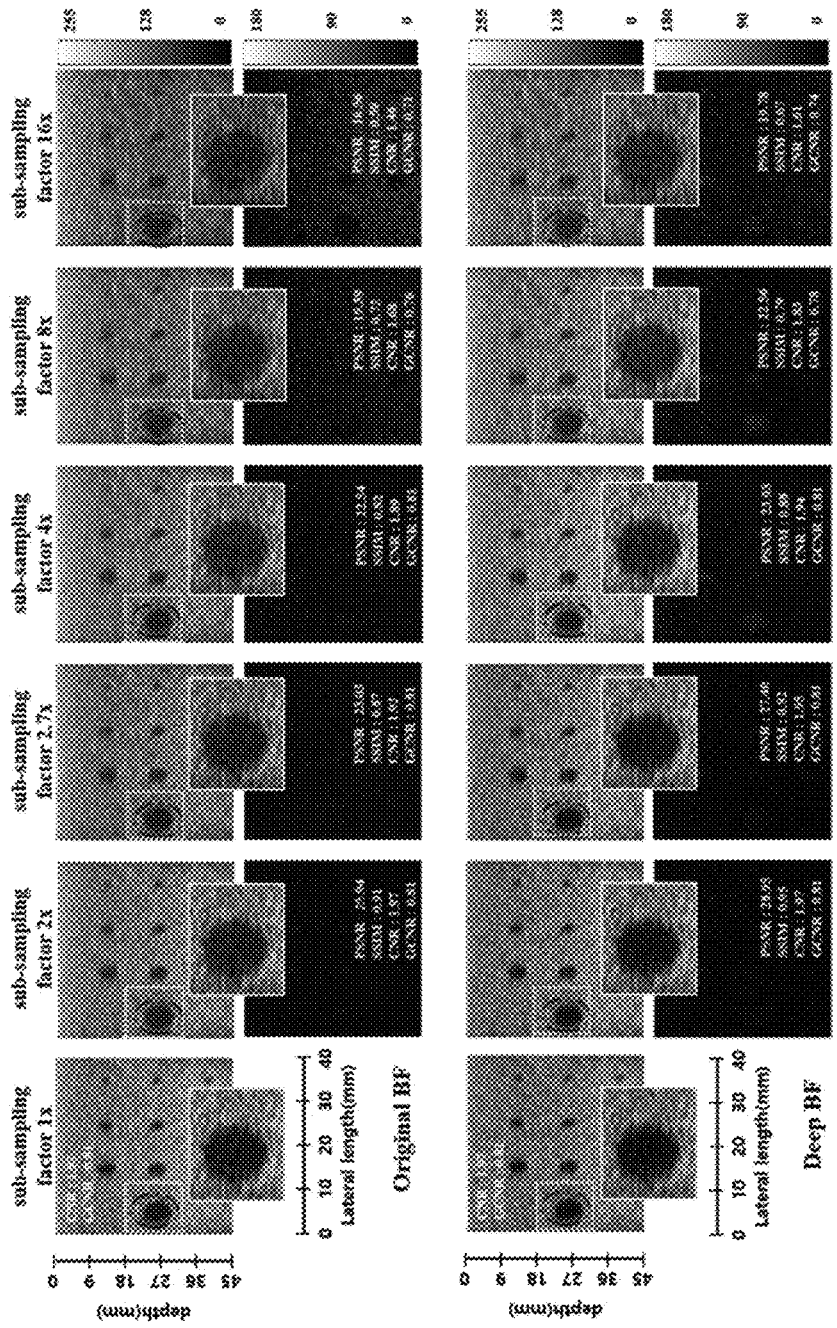
FIGS. 6A and 6B are drawings illustrating reconstruction results of a standard DAS beamformer and a method according to an embodiment of the inventive concept for the phantom with respect to two sub-sampling schemes.
Figure 6B:
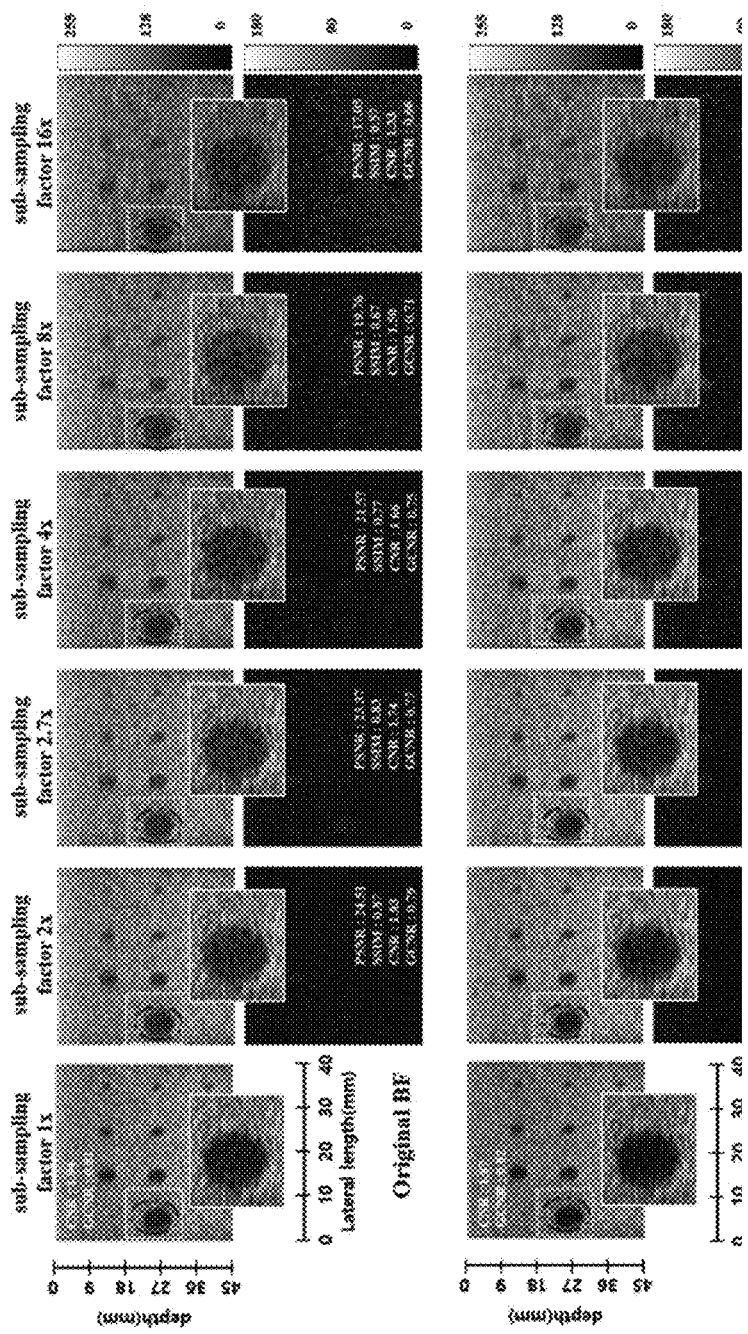

FIGS. 6A and 6B are drawings illustrating reconstruction results of a standard DA beamformer and a method according to an embodiment of the inventive concept for the phantom with respect to two subsampling schemes. FIGS. 6A and 6B illustrate reconstruction results of phantom data at 1×, 2×, 2.7×, 4×, 8×, and 16× acceleration using both sub-sampling schemes, that is, a variable sampling scheme (FIG. 6A) and a fixed sampling scheme (FIG. 6B).

As may be observed in FIGS. 6A and 6B, by harnessing the spatio-temporal (multi-depth and multi-line) learning, the CNN-based beam-former according to an embodiment of the inventive concept successfully reconstructs the images with good quality in all downsampling schemes. CNN automatically identifies the missing RF data and approximates it with available neighboring information. Furthermore, the network according to an embodiment of the inventive concept is trained on the variable sampling scheme only, however, the relative improvement in both schemes in test phase is nearly the same for both sampling schemes. This shows the generalization power of the method according to an embodiment of the inventive concept.

As such, the method according to embodiments of the inventive concept may stably perform interpolation in any sampling pattern using a deep learning technology and may provide a good-quality image, thus replacing a conventional DAS beamformer.

Furthermore, the method according to embodiments of the inventive concept may reconstruct a high-quality ultrasound image through a data cube received using a small number of sensors, thus being applicable to all ultrasound systems or devices which reconstruct a high-quality image using a small number of sensors.

Furthermore, in the method according to embodiments of the inventive concept, a single universal deep beamformer, which is trained using a purely data-centric method, may generate an enhanced image in a wide variety of apertures and channel sub-sampling patterns.

Furthermore, the method according to embodiments of the inventive concept may provide better interpolation performance than interpolation performance of a general beamformer using a deep learning-based neural network.

In addition, the method according to embodiments of the inventive concept is described such that the neural network performs the signal adder function and the Hilbert transform function, but is not limited thereto. For example, the neural network may be trained to perform at least one of the signal adder function or the Hilbert transform function. For example, the neural network may be trained to perform only the Hilbert transform function, thus performing the signal adder function using separate signal processing. In other words, the method according to another embodiment of the inventive concept may perform a signal adding process using a signal adder after being transformed into focus data and may then perform the Hilbert transform function using the neural network to output IQ data, thus detecting an envelope of the output IQ data and reconstructing a high-quality ultrasound image through a log compression process.

Figure 7:
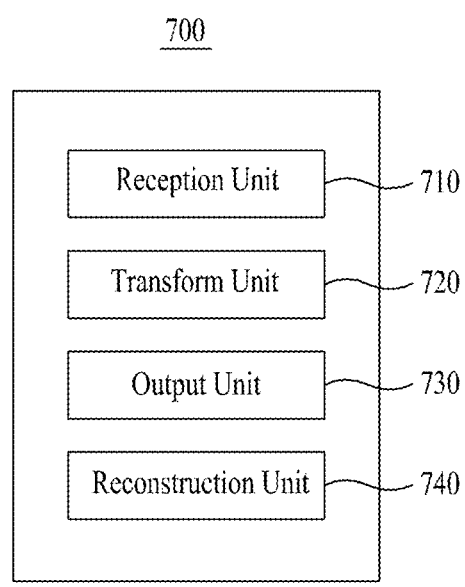
FIG. 7 is a block diagram illustrating a configuration of an apparatus for processing an ultrasound image according to an embodiment of the inventive concept.

FIG. 7 is a block diagram illustrating a configuration of an apparatus for processing an ultrasound image according to an embodiment of the inventive concept. FIG. 7 illustrates a configuration of a device which performs the method of FIGS. 1 to 6B.

Referring to FIG. 7, the apparatus 700 for processing the ultrasound image according to an embodiment of the inventive concept may include a reception unit 710, a transform unit 720, an output unit 730, and a reconstruction unit 740.

The reception unit 710 may receive ultrasound raw data, for example, a data cube, via sensors included in an ultrasound imaging system, that is, sensors included in a receiver, for example, 16 receiver sensors.

Herein, the data cube may include an index or identification number each of the receiver sensors, a transmit event (TE), and depth information.

The transform unit 720 may transform the received data cube into focus data through beam focusing.

The output unit 730 may output inphase data and quadrature phase data for the focus data using a neural network corresponding to signal adder and Hilbert transform functions.

In this case, the neural network may include a convolutional neural network (CNN), a convolutional framelet-based neural network, or a multi-resolution neural network, and may include a bypass connection from an encoder part for performing encoding to a decoder part for performing decoding.

In this case, the neural network may perform interpolation independently of a sampling pattern to output inphase data and quadrature phase data for reconstructing a high-quality ultrasound image. Such a neural network may be trained using a predetermined training data set to generate a learning model corresponding to the signal adder and Hilbert transform functions. For example, the neural network may be trained using a data cube including three or more depths to generate the learning model corresponding to the signal adder and Hilbert transform functions. The output unit 730 may output the inphase data and the quadrature phase data for the focus data using the neural network of the generated learning model.

The reconstruction unit 740 may detect an envelope of the inphase data and the quadrature phase data and may reconstruct an ultrasound image for the data cube using log compression.

It is apparent to those skilled in the art that, although the description is omitted in the apparatus 700 for processing the ultrasound image in FIG. 7, the respective components configuring FIG. 7 may include all details described in FIGS. 1 to 6B.

The foregoing devices may be realized by hardware elements, software elements and/or combinations thereof. For example, the devices and components illustrated in the exemplary embodiments of the inventive concept may be implemented in one or more general-use computers or special-purpose computers, such as a processor, a controller, an arithmetic logic unit (ALU), a digital signal processor, a microcomputer, a field programmable array (FPA), a programmable logic unit (PLU), a microprocessor or any device which may execute instructions and respond. A processing unit may implement an operating system (OS) or one or more software applications running on the OS. Further, the processing unit may access, store, manipulate, process and generate data in response to execution of software. It will be understood by those skilled in the art that although a single processing unit may be illustrated for convenience of understanding, the processing unit may include a plurality of processing elements and/or a plurality of types of processing elements. For example, the processing unit may include a plurality of processors or one processor and one controller. Also, the processing unit may have a different processing configuration, such as a parallel processor.

Software may include computer programs, codes, instructions or one or more combinations thereof and may configure a processing unit to operate in a desired manner or may independently or collectively control the processing unit. Software and/or data may be permanently or temporarily embodied in any type of machine, components, physical equipment, virtual equipment, computer storage media or units or transmitted signal waves so as to be interpreted by the processing unit or to provide instructions or data to the processing unit. Software may be dispersed throughout computer systems connected via networks and may be stored or executed in a dispersion manner Software and data may be recorded in one or more computer-readable storage media.

The methods according to the above-described exemplary embodiments of the inventive concept may be implemented with program instructions which may be executed through various computer means and may be recorded in computer-readable media. The media may also include, alone or in combination with the program instructions, data files, data structures, and the like. The program instructions recorded in the media may be designed and configured specially for the exemplary embodiments of the inventive concept or be known and available to those skilled in computer software. Computer-readable media include magnetic media such as hard disks, floppy disks, and magnetic tape; optical media such as compact disc-read only memory (CD-ROM) disks and digital versatile discs (DVDs); magneto-optical media such as floptical disks; and hardware devices that are specially configured to store and perform program instructions, such as read-only memory (ROM), random access memory (RAM), flash memory, and the like. Program instructions include both machine codes, such as produced by a compiler, and higher level codes that may be executed by the computer using an interpreter.

According to embodiments of the inventive concept, the apparatus for processing the ultrasound image may stably perform interpolation in any sampling pattern using a deep learning technology and may provide a good-quality image, thus replacing a conventional delay-and-sum (DAS) beamformer.

An ultrasound device is a medical device incapable of being replaced in cardiac imaging or fetal imaging in the sense that there is no risk of radiation exposure and it is able to perform real-time imaging. In particular, recently, there has been a need for technologies of providing a good-quality image using a small number of sensors in high-speed 3-D ultrasound imaging and low-power ultrasound imaging. Thus, embodiments of the inventive concept may be applied to all ultrasound systems or devices which reconstruct a high-quality image using a small number of sensors.

According to embodiments of the inventive concept, a single universal deep beamformer, which is trained using a purely data-centric method, may generate an enhanced image in a wide variety of apertures and channel sub-sampling patterns.

Embodiments of the inventive concept are applicable to a portable ultrasound device system and very-high-speed low-power ultrasound system, and may provide better interpolation performance than interpolation performance of a general beamformer using a deep learning-based neural network and may more enhance contrast of an original image. Particularly, embodiments of the inventive concept may generate a high-quality ultrasound image using a single beamformer by designing an end-to-end deep learning framework capable of directly processing sub-sampling RF data obtained with different sub-sampling rates and different detector configurations.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

Therefore, other implements, other embodiments, and equivalents to claims are within the scope of the following claims.

What is claimed is:

1. A method for processing an ultrasound image, the method comprising:
   receiving a data cube via sensors;
   transforming the received data cube into focus data through beam focusing; and
   outputting inphase data and quadrature phase data for the focus data using a neural network corresponding to signal adder and Hilbert transform functions,
   wherein the neural network performs interpolation independently of a sampling pattern to output the inphase data and the quadrature phase data for reconstructing a high-quality ultrasound image.

2. The method of claim 1, further comprising:
   detecting an envelope of the inphase data and the quadrature phase data and reconstructing an ultrasound image for the data cube using log compression.

3. The method of claim 1, wherein the neural network is trained using a data cube using at least three or more depths to generate a learning model corresponding to the signal adder and Hilbert transform functions and output the inphase data and the quadrature phase data for the focus data using the learning model.

4. The method of claim 1, wherein the neural network includes a convolutional framelet-based neural network.

5. The method of claim 1, wherein the neural network includes a bypass connection from an encoder part to a decoder part.

6. A method for processing an ultrasound image, the method comprising:
   receiving a data cube via sensors;
   transforming the received data cube into focus data through beam focusing;
   adding signals of the transformed focus data; and
   outputting inphase data and quadrature phase data for focus data of the added signal using a neural network corresponding to a Hilbert transform function,
   wherein the neural network performs interpolation independently of a sampling pattern to output the inphase data and the quadrature phase data for reconstructing a high-quality ultrasound image.

7. The method of claim 6, further comprising:
   detecting an envelope of the inphase data and the quadrature phase data and reconstructing an ultrasound image for the data cube using log compression.

8. An apparatus for processing an ultrasound image, the apparatus comprising:
   a reception unit configured to receive a data cube via sensors;
   a transform unit configured to transform the received data cube into focus data through beam focusing; and
   an output unit configured to output inphase data and quadrature phase data for the focus data using a neural network corresponding to signal adder and Hilbert transform functions,
   wherein the neural network performs interpolation independently of a sampling pattern to output the inphase data and the quadrature phase data for reconstructing a high-quality ultrasound image.

9. The apparatus of claim 8, further comprising:
   a reconstruction unit configured to detect an envelope of the inphase data and the quadrature phase data and reconstruct an ultrasound image for the data cube using log compression.

10. The apparatus of claim 8, wherein the neural network is trained using a data cube using at least three or more depths to generate a learning model corresponding to the signal adder and Hilbert transform functions and output the inphase data and the quadrature phase data for the focus data using the learning model.

11. The apparatus of claim 8, wherein the neural network includes a convolutional framelet-based neural network.

12. The apparatus of claim 11, wherein the neural network includes a bypass connection from an encoder part to a decoder part.

* * * * *